United States Patent
Ballam et al.

(10) Patent No.: US 10,258,267 B2
(45) Date of Patent: Apr. 16, 2019

(54) PULSE OXIMETER WITH AN ACCELEROMETER

(71) Applicant: CAPSULE TECHNOLOGIES, INC., San Diego, CA (US)

(72) Inventors: Robert Scott Ballam, Eatons Hill (AU); Robert Bruce Ganton, San Diego, CA (US)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 662 days.

(21) Appl. No.: 14/800,833

(22) Filed: Jul. 16, 2015

(65) Prior Publication Data

US 2016/0081601 A1  Mar. 24, 2016

Related U.S. Application Data (60) Provisional application No. 62/053,483, filed on Sep. 22, 2014.

(51) Int. Cl.
*A61B 5/1455* (2006.01)
*A61B 5/00* (2006.01)
*A61B 5/11* (2006.01)

(52) U.S. Cl.
CPC ........ *A61B 5/14551* (2013.01); *A61B 5/1118* (2013.01); *A61B 5/14552* (2013.01); *A61B 5/6826* (2013.01); *A61B 5/6832* (2013.01); *A61B 5/6833* (2013.01); *A61B 5/721* (2013.01); *A61B 5/7289* (2013.01); *A61B 5/7221* (2013.01); *A61B 2560/0209* (2013.01); *A61B 2562/0219* (2013.01)

(58) Field of Classification Search
CPC .............. A61B 5/1455; A61B 5/14551; A61B 5/14552; A61B 5/6832; A61B 5/721
See application file for complete search history.

(56) References Cited

U.S. PATENT DOCUMENTS

| 5,025,791 A | 6/1991 | Niwa |
| 5,924,979 A | 7/1999 | Swedlow et al. |
| 6,763,256 B2 * | 7/2004 | Kimball ............ A61B 5/14551 600/336 |

(Continued)

FOREIGN PATENT DOCUMENTS

| WO | 03003914 A1 | 1/2003 |
| WO | 2011010244 A1 | 1/2011 |

(Continued)

OTHER PUBLICATIONS

International Search Report and Written Opinion—PCT/US2015/040832—ISA/EPO—Sep. 28, 2015.

*Primary Examiner* — Eric F Winakur (57) ABSTRACT

Systems, methods, and devices of the various embodiments provide a pulse oximeter capable of taking blood oxygen readings based on readings from an accelerometer. The various embodiments may provide an electronic patch including a pulse oximeter and accelerometer connected to a processor, wherein the processor is configured with processor executable instructions to control the operation of the pulse oximeter based at least in part on data received from the accelerometer. In various embodiments the electronic patch may further include a coin cell battery, or other low power source, that may power the pulse oximeter.

11 Claims, 9 Drawing Sheets

(56) References Cited

U.S. PATENT DOCUMENTS

| | | |
|---|---|---|
| 8,764,651 B2 | 7/2014 | Tran |
| 2005/0228298 A1* | 10/2005 | Banet .................. A61B 5/1455 600/323 |
| 2009/0247849 A1* | 10/2009 | McCutcheon ..... A61B 5/14551 600/323 |
| 2010/0324384 A1 | 12/2010 | Moon et al. |
| 2013/0030259 A1* | 1/2013 | Thomsen ............. A61B 5/6833 600/301 |
| 2013/0274565 A1 | 10/2013 | Langer et al. |
| 2014/0088660 A1 | 3/2014 | Debardi et al. |
| 2015/0011854 A1* | 1/2015 | Frix ................... A61B 5/14551 600/364 |

FOREIGN PATENT DOCUMENTS

| | | |
|---|---|---|
| WO | 2012020433 A1 | 2/2012 |
| WO | 2014066059 A1 | 5/2014 |

\* cited by examiner

PULSE OXIMETER WITH AN ACCELEROMETER

RELATED APPLICATIONS

The present application claims priority to U.S. Provisional Patent Application No. 62/053,483 entitled "Improved Pulse Oximeter Readings With An Accelerometer," filed Sep. 22, 2014, the entire contents of which are hereby incorporated by reference.

BACKGROUND

Continuous monitoring of vital signs with the ability to remotely monitor patient status is a growing field and the ability to incorporate multiple measurement capabilities into a single small unobtrusive patch that can be worn by a patient (i.e., a body worn patch) for multiple days at a time is a desirable feature. One such measurement is blood oxygen reading, often carried out by a pulse oximeter. Current pulse oximeter designs use a high precision current sink to control light emitting diodes (LED's) which are driven with a voltage controlled source. A patient's blood oxygen reading may be influenced by the patient's level of activity, and therefore measurements that may be taken by a patch may be misleading if the readings are provided with no context regarding the patient's activities.

SUMMARY

The systems, methods, and devices of the various embodiments provide a pulse oximeter capable of taking blood oxygen readings based on, or informed by, data from an accelerometer. The various embodiments provide an electronic patch including a pulse oximeter and an accelerometer connected to a processor, in which the processor is configured with processor executable instructions to control the operation of the pulse oximeter based at least in part on data from the accelerometer. In various embodiments, the electronic patch may further include a coin cell battery, or other low power source, that may power the pulse oximeter.

In an embodiment, the pulse oximeter may be controlled to generate light and/or measure light by the processor based at least in part on the measurements received from the accelerometer. In an embodiment, the processor may determine active and/or rest states of a patient based at least in part on the measurements from the accelerometer and may only turn on the pulse oximeter and operate the pulse oximeter during rest periods to increase the accuracy of the oxygen measurements and pulse measurements and reduce power consumption. In an additional embodiment, the accelerometer data may be used by the processor to indicate the accuracy of the pulse oximeter readings, for example by indicating whether a reading was taken during a period of high patient movement or a low patient movement.

In a further embodiment, the accelerometer data may be used by the processor to identify rest and/or sleep times and lower the measurement rate of the pulse oximeter during rest and/or sleep times to improve (e.g., reduce) power source consumption during rest and/or sleep times. In an embodiment, the accelerometer data may be used by the processor to target blood oxygen measurements and pulse measurements to correspond to low and/or high (e.g., peak) activity. Enabling the patch processor to identify rest and/or high (e.g., peak) activity as well as measure blood oxygen levels and pulse in a single device (e.g., one electronic patch) may allow for significant diagnostic capabilities. In an embodiment, an increase in heart rate measured by the pulse oximeter may be compared with accelerometer data by the processor to determine whether the increase is activity or stress related.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The terms "computing device" are used herein to refer to any one or all of cellular telephones, smart-phones, web-pads, tablet computers, Internet enabled cellular telephones, Wi-Fi enabled electronic devices, laptop computers, personal computers, and similar electronic devices equipped with at least a processor and configured to communicate with an electronic patch described herein.

Pulse oximeters monitor oxygen levels in the blood stream. Pulse oximeters typically operate by shining light of two different wavelengths through a body part (e.g., from a red LED and infrared LED) and measuring (e.g., via phototransistor) the relative differences in the amplitude of the original light and the received light at the two different wavelengths. For example, one wavelength may be red and the other infrared. Blood with lower levels of oxygen may tend to absorb less infrared light and more red light. Alternatively, blood with higher levels of oxygen may tend to absorb more infrared light and less red light. Thus, a properly calibrated pulse oximeter may determine oxygen levels by emitting light of red and infrared wavelengths and measuring the relative amounts of red and infrared light after the light has passed through a body part, such as a fingertip or earlobe. Additionally, the measurement of the received light may also enable the determination of heart rate for the patient by the pulse oximeter. The movement of the patient may result in degradation of the blood oxygen measurements and heart rate measurements by a pulse oximeter.

Current pulse oximeters have large power requirements and would require large batteries unsuitable for use in electronic patches. Thus, improvements to pulse oximeters to reduce the power requirements of the pulse oximeters, such as to a level low enough to allow coin cell batteries to power the pulse oximeters, are needed to support integrating pulse oximeters onto patient worn electronic patches.

The systems, methods, and devices of the various embodiments provide a pulse oximeter capable of taking blood oxygen readings based on, or informed by, readings from an accelerometer. The various embodiments may provide an electronic patch including a pulse oximeter and accelerometer connected to a processor, wherein the processor is configured with processor executable instructions to control the operation of the pulse oximeter based at least in part on measurements from the accelerometer. In various embodiments, the electronic patch may further include a coin cell battery, or other low power source, that may power the pulse oximeter.

In an embodiment, the pulse oximeter may be controlled to generate light and/or measure light by the processor based at least in part on the measurements received from the accelerometer. In an embodiment, the processor may determine active and/or rest states of a patient based at least in part on the measurements from the accelerometer and may only turn on and operate the pulse oximeter during rest periods to increase the accuracy of the oxygen measurements and pulse measurements and reduce power consumption. Rest states and/or active states may be states indicating a relative activity level of a patient. For example, a patient in a rest state may be less active (e.g., moving less) than the patient in the active state. In the various embodiments, a rest state may indicate a patient is still or is moving less than a threshold value representing a maximum amount of motion allowed in the rest state. An amount of motion above the threshold value may indicate the patient is in an active state and not in a rest state. In this manner, though a patient may not be perfectly still, his or her motion may be below the threshold value, thereby indicating the patient may be in the rest state despite some level of motion being registered by an accelerometer.

In an additional embodiment, the accelerometer data may be used by the processor to indicate the accuracy of the pulse oximeter readings, for example by indicating the reading was or was not taken during a period of high patient movement. In a further embodiment, the accelerometer data may be used by the processor to identify rest and/or sleep times and lower the measurement rate of the pulse oximeter during rest and/or sleep times to improve (e.g., reduce) power source consumption during rest and/or sleep times. In an embodiment, the data may be used by the processor to focus blood oxygen measurements and pulse measurements to correspond to low and/or high (e.g., peak) activity. Enabling the ability to identify rest and/or high (e.g., peak) activity, as well as measure blood oxygen levels and pulse in a single device (e.g., one electronic patch), may allow for significant diagnostic capabilities. In an embodiment, an increase in heart rate measured by the pulse oximeter may be compared with data by the processor to determine whether the increase is activity or stress related.

In various embodiments, the processor of an electronic patch may turn on and operate the pulse oximeter periodically. In an embodiment, a processor of an electronic patch may monitor a status of a timer, such as a measurement period timer indicating a minimum time period to wait between attempting pulse oximeter measurements. In response to determining that the status of the timer indicates a time to attempt a pulse oximeter measurement is reached, the processor may determine active and/or rest states of a patient based at least in part on the measurements from the accelerometer. In response to determining that the measurements from the accelerometer indicate a rest state of the patient is reached, the processor may turn on and operate the pulse oximeter to increase the accuracy of the oxygen measurements and pulse measurements and reduce power consumption. After the oxygen measurements and pulse measurements are taken, the processor may turn off the pulse oximeter and continue to monitor the status of the timer to determine when the next pulse oximeter measurement should be attempted. In a further embodiment, the processor may use a second timer to determine when to determine the active and/or rest states of a patient, such as a window countdown timer indicating a maximum time period to wait for a patient to enter a rest state. In response to determining that the status of the second timer indicates a time to wait to attempt a pulse oximeter measurement is exceeded, the processor may turn on and operate the pulse oximeter regardless of the current state of the patient.

Figure 1:
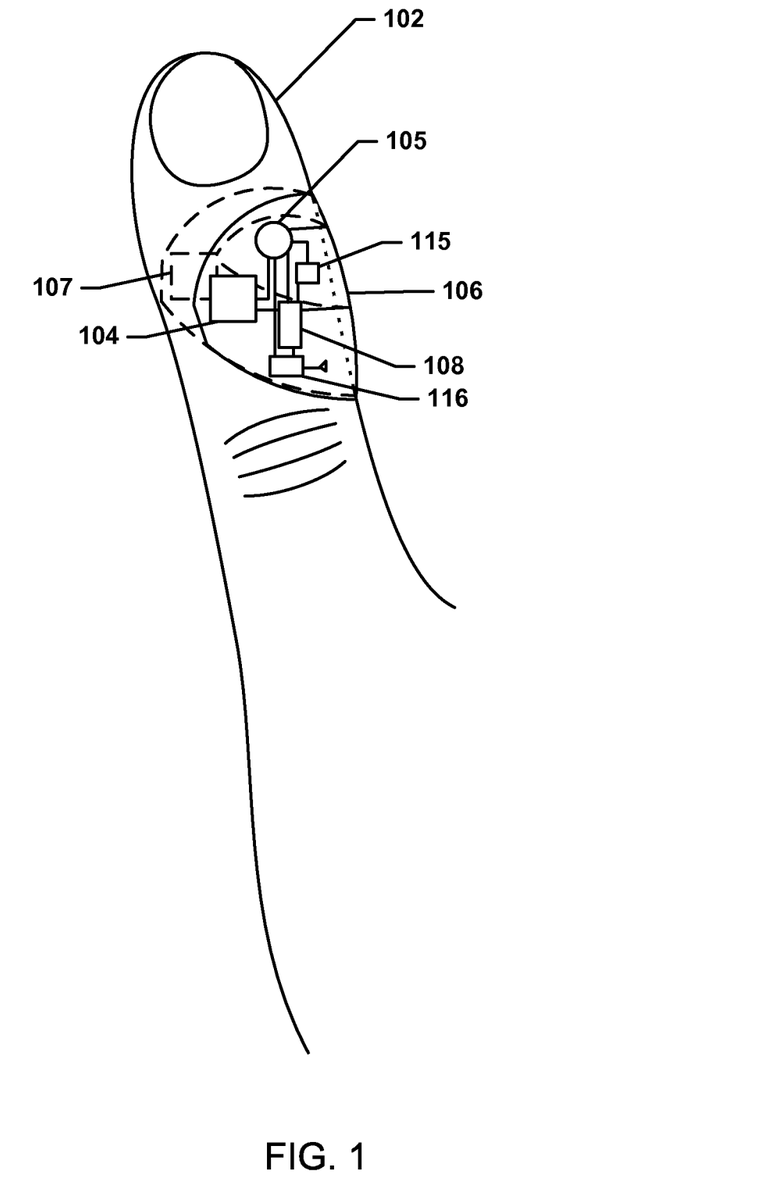
FIG. 1 is a component block diagram illustrating an embodiment electronic patch including a pulse oximeter and accelerometer placed on a patient.

FIG. 1 illustrates an embodiment electronic patch 106 including a pulse oximeter placed on a patient 102, such as on a skin surface of a finger of a patient 102. In various embodiments, an electronic patch 106 may be flexible and resilient so that placement and removal of the electronic patch 106 from the patient 102 does not damage the electronic patch 106. The electronic patch 102 may include a pulse oximeter circuit comprised of a light output circuit 104 (e.g., a circuit including one or more LEDs that output light) and a light receiver circuit 107 (e.g., a circuit including one or more phototransistor) configured to measure light transmitted through the patient's skin and tissue emitted by the light output circuit 104, and a processor 108 connected to the light output circuit 104 and light receiver circuit 107 configured with processor executable instructions to control the operations of and/or receive measurements from the pulse oximeter (e.g., the light output circuit 104 and/or the light receiver circuit 107). In an embodiment, the processor 108 may be further configured with processor executable instructions to determine the patient's 102 blood oxygen level and/or pulse based on the measurements from the pulse oximeter (e.g., the light output circuit 104 and/or the light receiver circuit 107). In an embodiment, the light output circuit 104, the light receiver circuit 107, and/or the processor 108 may be connected to a low power source 105, such as a coin cell battery.

In an embodiment, the electronic patch 106 may also include at least one accelerometer 115 connected to the processor 108 and the low power source 105. The processor 108 may receive acceleration measurements from the accelerometer 115 and may be configured with processor executable instructions to turn on and/or off the accelerometer 115 and to control the operations of the pulse oximeter (e.g., the light output circuit 104 and/or the light receiver circuit 107) based at least in part on the measurements received from the accelerometer 115. In various embodiments, the accelerometer 115 may remain on once the patch is activated or powered up/on, and continually draw current from the low power source 105. The accelerometer 115 may draw an amount of current that is relatively smaller than the amount of current drawn by the pulse oximeter (e.g., the light output circuit 104 and/or the light receiver circuit 107). While the accelerometer 115 may continually operate, the processor 108 may intermittently turn on and off the pulse oximeter (e.g., the light output circuit 104 and/or the light receiver circuit 107) to reduce the total amount of current drawn from the low power source 105 compared with continually leaving the pulse oximeter (e.g., the light output circuit 104 and/or the light receiver circuit 107) on. For example, the accelerometer 115 may draw 0.5 microamperes of current in a low power mode and the pulse oximeter (e.g., the light output circuit 104 and/or the light receiver circuit 107) may draw 20 milliamperes of current. In such an example electronic patch 106, only turning on the pulse oximeter (e.g., the light output circuit 104 and/or the light receiver circuit 107) intermittently, such as only when a patient is in a rest state such that measurements would be accurate, may extend the life of the low power source 105, such as a coin cell battery, compared to the life of the low power source 105 that could be achieved with the pulse oximeter always on.

Accelerometer data may be sampled acceleration measurements provided by the accelerometer 115 or interrupts received from the accelerometer 115 indicating a threshold meeting or exceeding acceleration event (e.g., a peak acceleration event) was detected by the accelerometer. When accelerometer data are sampled acceleration measurements provided by the accelerometer 115, the processor 108 may analyze the acceleration measurements and make determinations based on the received acceleration data. When accelerometer data are interrupts signaled by the accelerometer 115, the processor 108 may analyze the interrupt that was signaled and make determinations based on the type of interrupt received. Receiving interrupts from the accelerometer 115 may be a lower power alternative to receiving and processing acceleration measurements by the processor 108.

The electronic patch 106 may also include a transceiver 116 connected to an antenna and the processor 108 and the low power source 105. In this manner, via the transceiver 116 and antenna, the processor 108 may establish wireless connections, e.g., Bluetooth® connections, with remote devices, such as a smart phone, and may exchange data with the remote devices. The transceiver 116 is used merely as an example of one type of wireless connection device suitable for use in the various embodiments, in other configurations receivers and/or transmitters, separately or in conjunction may be substituted for transceiver 116 to provide transmission and/or reception capabilities to the processor 108 as needed for various different use cases for the electronic patch 106.

Figure 2:
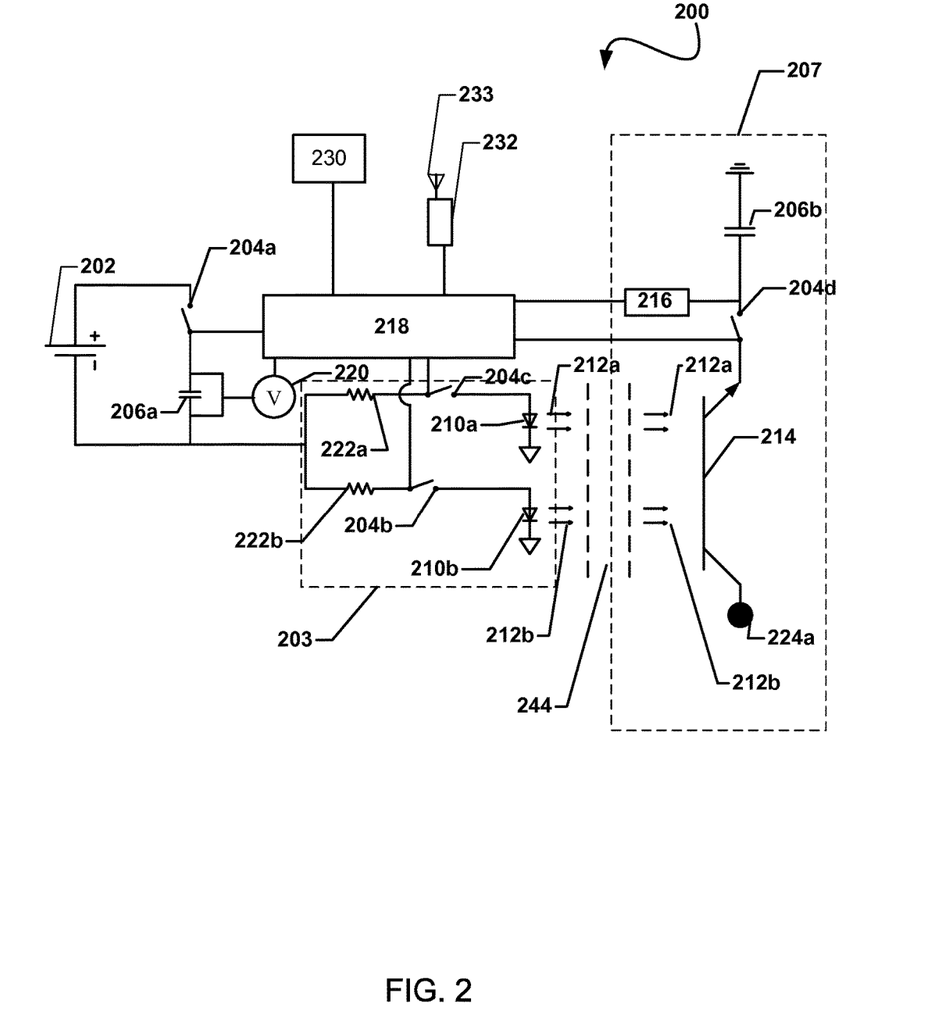
FIG. 2 is a circuit diagram illustrating an embodiment circuit for a pulse oximeter and accelerometer that may be suitable for inclusion on an electronic patch.

FIG. 2 is a circuit diagram illustrating an embodiment circuit 200 for a pulse oximeter including an accelerometer 230. In an embodiment, the circuit 200 may be integrated into an electronic patch worn by a patient, such as the electronic patch 106 described above. A low voltage power source may power the processor 218 or the processor may be powered by a separate power source (not shown). The low voltage source 202 powers the capacitor 206a when the switch 204a is closed. The switch may be located anywhere on the loop containing the low voltage source 202 and switch 204a, provided it can electrically separate the low voltage source 202 and switch 204a. The processor 218 may control when the switch 204a opens or closes. For example, the processor 218 may close switch 204a to allow capacitor 206a to collect electric charge. The charge on the capacitor 206a may correspond via a known relationship to the voltage across the capacitor 206a. The voltage across the capacitor 206a may be monitored by the voltmeter 220. The voltmeter 220 may report the measured voltage to processor 218.

When the voltage across capacitor 206a reaches a predetermined limit, the processor 218 may open switch 204a at an appropriate time to provide power to a light output circuit 203 to cause the light output circuit 203 to generate light. As an example, light output circuit 203 may include switches 204b and 204c and a red LED 210a and infrared LED 210b. The processor 218 may close switches 204b, 204c to allow charge to flow from capacitor 206a to red LED 210a and infrared LED 210b. The switches 204b and 204c may be closed consecutively to measure the different wavelength absorption rates in quick succession. Switches 204b, 204c may remain open while the capacitor is charging to prevent unnecessary drain on the low voltage source 202. Resistors 222a, 222b may be connected in series with a red LED 210a and an infrared LED 210b to control the current passing through each LED 210a, 210b. The resistors 222a, 222b may have the same or different resistances than each other. The resistors 222a, 222b may provide greater control on the allocation of current from the capacitor 206a, thus helping to eliminate the need for higher-current power supplies. In an embodiment, the switches 204b, 204c may be closed by the processor 218 to provide charge from the capacitor 206a to the red LED 210a and infrared LED 210b for a period of time to cause the LEDs 210a and 210b to emit red light 212a and infrared light 212b, respectively. After the period of time the switches 204b, 204c may be opened by the microprocessor 218 to isolate the LEDs 210a and 210b from the capacitor 206a to stop providing charge from the capacitor 206a to the LEDs 210a and 210b and stop the LEDs 210a and 210b from emitting red light 212a and infrared light 212b, respectively. In this manner, light bursts may be generated from the red LED 210a and infrared LED 210b, and the current draw of the circuit 200 may be minimized by only turning the red LED 210a and infrared LED 210b on for the period of time.

When sufficient current passes through the red LED 210a and infrared LED 210b, they emit red light 212a and infrared light 212b, respectively. The light 212a, 212b propagates through a body part 244, such as a fingertip or earlobe. The amount of light absorbed by the body part 244 may be a function of the amount of oxygen in the blood and the amount of blood in the body part 244 at the time of sampling. Specifically, a body part 244 with a relatively large amount of oxygen may tend to absorb more infrared light 212b and less red light 212a. A body part 244 with a relatively small amount of oxygen may tend to absorb less infrared light 212b and more red light 212a. After passing through the body part 244, the red light 212a and infrared light 212b may be absorbed by a photodetector 214, such as a phototransistor or a light sensor, of a light receiver circuit 207 comprised of the photodetector 214, a switch 204d, a capacitor 206b, and an A/D converter 216. Analysis of the absolute amplitude of the detected light signal as well as the relative amplitudes of the detected red light 212a and detected infrared light 212b may reveal various properties of the blood, such as the pulse profile and the amount of oxygen in the blood.

The photodetector 214 may be powered by voltage source 224a. Processor 218 may control switch 204d. When the switch 204d is open, current may not flow from the photodetector 214 and data may not be collected. When the switch 204d is closed, the photodetector 214 may transfer data to the microprocessor 218. The microprocessor may synchronize the opening and closing of switch 204d with switches 204a, 204b, 204c such that switch 204d is only closed when the photodetector 214 intercepts the light 212a, 212b. Power demand may be further reduced by leaving the switch 204d open when the photodetector is not receiving useful data. When the switch 204d is closed, current may flow from the photodetector 214 to the capacitor 206b and be stored in the capacitor 206b at the input to the A/D converter 216. The A/D converter 216 may measure the voltage at the capacitor 206b and transfer the data to the microprocessor 218. In an embodiment, the on periods of the red LED 210a and infrared LED 210b may be synchronized with the opening and closing of switch 204d by microprocessor 218. The microprocessor 218 may close the switch 204d to allow the photodetector 214 to start integrating its received signal just before the red LED 210a and infrared LED 210b are turned on by discharging the capacitor 206a, and may control the A/D converter 216 to take a voltage measurement as soon as the red LED 210a and infrared LED 210b are off. In an embodiment, the photodetector 214 may be a single device and may comprise two separate detectors tuned separately for each wavelength of light in use. The digital output of the A/D converter 216 may be the output of the light receiver circuit 207 which may be analyzed by the processor 218 as measurements of the blood oxygen level.

In an embodiment, the processor 218 may also be connected to the accelerometer 230 and may receive acceleration measurements from the accelerometer 230 and may be configured with processor executable instructions to control the operations of the switches 204a, 204b, 204c, and/or 204d to turn the light output circuit 203 and/or the light receiver circuit 207 on and/or off, respectively, based at least in part on the measurements received from the accelerometer 230. In this manner, the light output circuit 203 may be turned on and/or off and controlled to generate light, and/or the light receiver circuit 207 may be turned on and/or off and controlled to receive and measure light by the processor 218 based at least in part on the measurements received from the accelerometer 230. For example, the processor 218 may be configured with processor executable instructions to determine active and/or rest states of a patient based at least in part on the measurements from the accelerometer 230 and may only operate the light output circuit 203 and/or light receiver circuit 207 during rest periods to increase the accuracy of the oxygen measurements and pulse measurements and reduce power consumption. In an additional embodiment, the accelerometer 230 measurements may be used by the processor 218 to indicate the accuracy of the pulse oximeter readings, for example by indicating the reading was or was not taken during a period of high patient movement.

In a further embodiment, the accelerometer 230 measurements may be used by the processor 218 to identify rest and/or sleep times and lower the measurement rate of the pulse oximeter during rest and/or sleep times to improve (e.g., reduce) low power source 202 consumption during rest and/or sleep times.

In an embodiment, the accelerometer 230 measurements may be used by the processor 218 to target blood oxygen measurements and pulse measurements to correspond to low and/or high (e.g., peak) activity. Enabling the ability to identify rest and/or high (e.g., peak) activity as well as measure blood oxygen levels and pulse in a single device (e.g., one electronic patch) may allow for significant diagnostic capabilities. A single patch design may be configured to operate in various combinations of embodiments described herein and therefore be customized for a particular need based on a per-patient diagnostic need related to the diagnostic purpose. In an embodiment, increases in the heart rate or changes in blood oxygen levels measured by the pulse oximeter may be compared with accelerometer data by the processor 218 to determine whether the changes are related to activity or stress.

A transceiver 232 may also be connected to an antenna 233 and the processor 218. In this manner, via the transceiver 232 and antenna 233, the processor 218 may establish wireless connections, e.g., Bluetooth® connections, with remote devices, such as a smart phone, and may exchange data with the remote devices.

Figure 3:
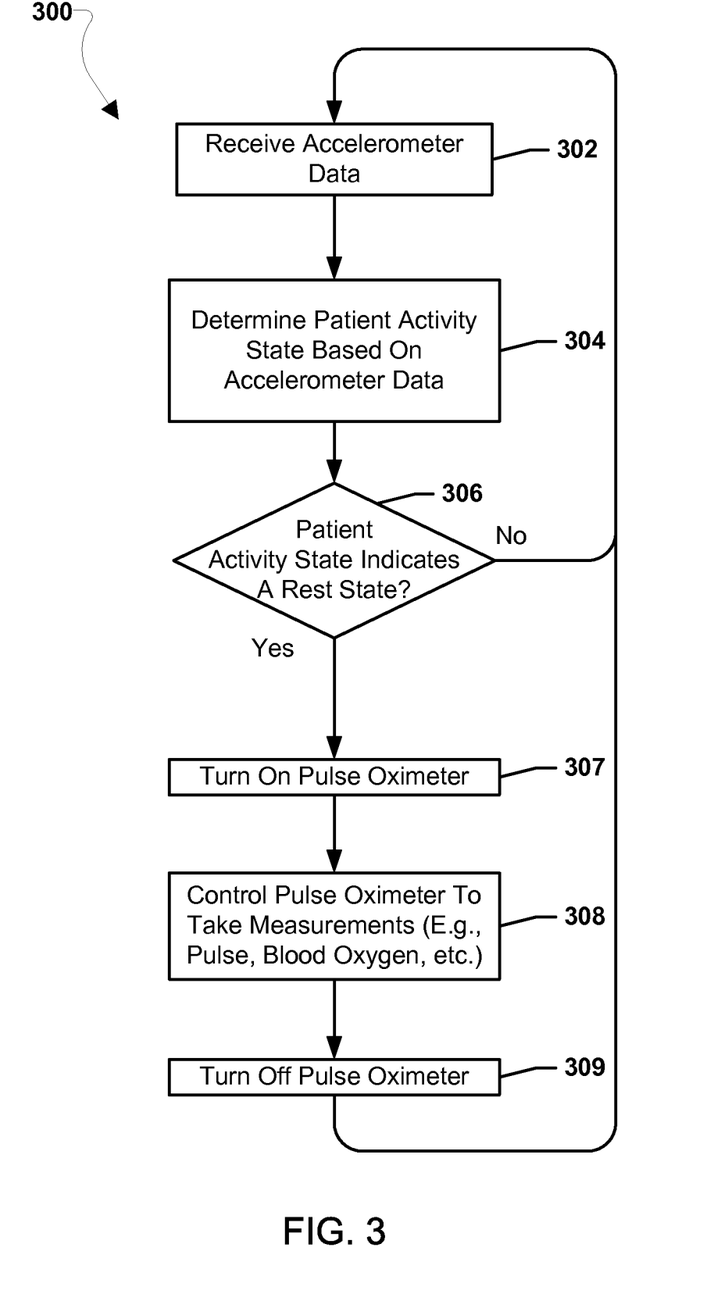
FIG. 3 is a process flow diagram illustrating an embodiment method for controlling a pulse oximeter based on a patient activity state indicated by accelerometer readings.

FIG. 3 illustrates an embodiment method 300 for controlling a pulse oximeter based on a patient activity state indicated by accelerometer readings. In an embodiment, the operations of method 300 may be performed by a processor of an electronic patch including a pulse oximeter and accelerometer, such as patch 106 described above. In block 302 the processor may receive accelerometer data from an accelerometer connected to the processor. Accelerometer Data may be sampled acceleration measurements provided by the accelerometer or interrupts received from the accelerometer indicating a threshold meeting or exceeding acceleration event (e.g., a peak acceleration event) was detected by the accelerometer. When accelerometer data are sampled acceleration measurements provided by the accelerometer, the processor may analyze the acceleration measurements and make determinations based on the received acceleration data. When accelerometer data are interrupts signaled by the accelerometer, the processor may analyze the interrupt signaled and make determinations based on the type of interrupt received. In block 304 the processor may determine a patient activity state based on the received accelerometer data. For example, the processor may determine whether the patient's activity state is at rest or active based on the received accelerometer data (e.g., when the accelerometer data are acceleration measurements by analyzing the acceleration measurements to determine whether the patient's activity state is at rest or active, when the accelerometer data are interrupts by analyzing the interrupts to determine whether interrupt signals a level of acceleration correlated with rest or active states, etc.). Rest and/or active states may be determined based on the received acceleration measurements (e.g., acceleration data and/or interrupt signals) by comparing the received acceleration measurements to threshold values associated with the rest and/or active states. For example, though some acceleration may be indicated for a patient (e.g., the patient may not be perfectly still), the level of acceleration may be below the threshold value for a rest state and the patient's activity state may still be determined to be a rest state.

In determination block 306 the processor may determine whether the patient's activity state indicates a rest state. In response to determining the patient's activity state is not indicated as a rest state (i.e., determination block 306="No"), the processor may continue to receive accelerometer data in block 302. In this manner, the pulse oximeter may not be activated when the patient is in an active state, thereby reducing the chance for erroneous measurements by the pulse oximeter and reducing the consumption of the power source because the pulse oximeter may not be activated when measurements are likely to be erroneous.

In response to determining that the patient activity state does indicate a rest state (i.e., determination block 306="Yes"), the processor may turn on the pulse oximeter in block 307. In this manner, the pulse oximeter may remain powered off and only draw current from a power source, such as a coin cell battery, when the patient activity state is indicated as a rest state based on accelerometer data. In block 308, the processor may control the pulse oximeter to take measurements, such as pulse rate measurements, blood oxygen measurements, etc. In this manner, the pulse oximeter may only be activated when the patient is in a rest state and the pulse oximeter measurements are more likely to be accurate, and thereby conserving power by limiting pulse oximeter activity. In block 309, the processor may turn off the pulse oximeter and perform the operations of the method 300 in a loop by receiving further accelerometer data block 302. In this manner, once a pulse oximeter measurement is taken, the pulse oximeter may be turned off to conserve power.

Figure 4:
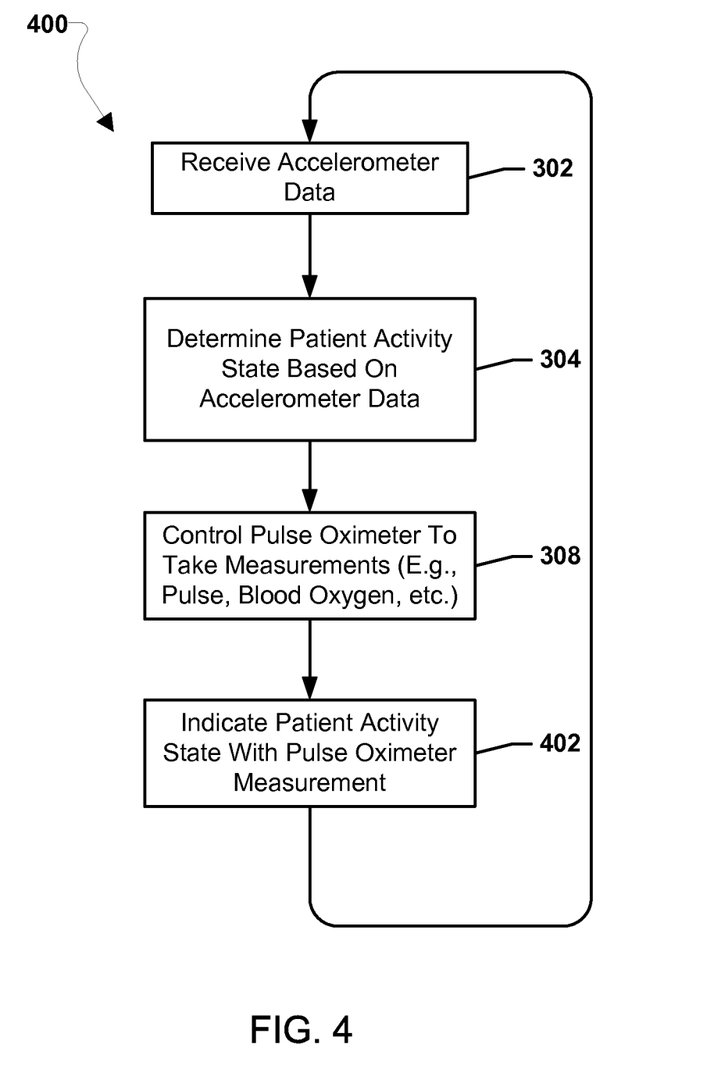
FIG. 4 is a process flow diagram illustrating an embodiment method for indicating an accuracy of pulse oximeter readings based on accelerometer readings.

FIG. 4 illustrates an embodiment method 400 for indicating an accuracy of pulse oximeter readings based on accelerometer readings. In an embodiment, the operations of method 400 may be performed by a processor of an electronic patch including a pulse oximeter and accelerometer, such as patch 106 described above. As described above, in block 302 the processor may receive accelerometer data and in block 304 the processor may determine a patient activity state based on the received accelerometer data. As described above, in block 308 the processor may control the pulse oximeter to take measurements, such as pulse rate measurements, blood oxygen measurements, etc.

In block 402, the processor may indicate the patient activity state with the pulse oximeter measurement. For example, the determined patient activity state, such as at rest or active, may be correlated with the pulse oximeter measurements in a memory, such as a measurement database. Upon indicating the patient activity state with the pulse oximeter measurements, the processor may repeat the method 400 in a loop by returning to perform the operations in block 302.

Figure 5:
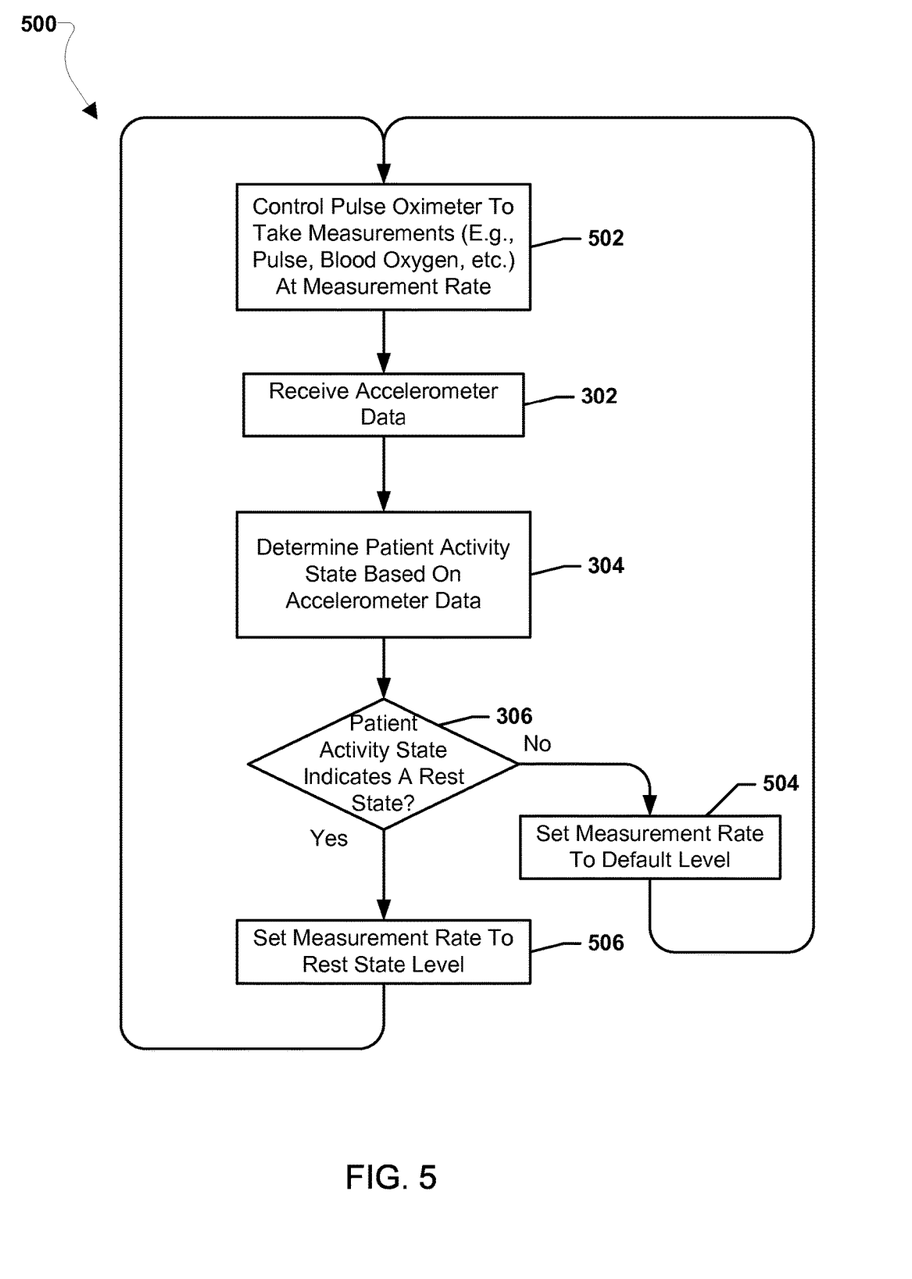
FIG. 5 is a process flow diagram illustrating an embodiment method for changing a pulse oximeter measurement rate based on a patient activity state indicated by accelerometer readings.

FIG. 5 illustrates an embodiment method 500 for changing a pulse oximeter measurement rate based on a patient activity state indicated by accelerometer readings. In an embodiment, the operations of method 500 may be performed by a processor of an electronic patch including a pulse oximeter and accelerometer, such as patch 106 described above. In block 502 the processor may control the pulse oximeter to take measurements, such as pulse rate measurements, blood oxygen measurements, etc., at a measurement rate. For example, a measurement rate may be a variable value (e.g., a sampling rate, such as measurements per minute) indicated in a memory and the processor may activate the pulse oximeter periodically according to the measurement rate. As described above, in block 302 the processor may receive accelerometer data and in block 304 the processor may determine a patient activity state based on the received accelerometer data.

As described above, in determination block 306 the processor may determine whether a patient activity state is a rest state. In response to determining the patient activity state is not a rest state (i.e., determination block 306="No"), the processor may set the measurement rate to a default level in block 504. For example the default level may be a relatively higher measurement rate, such as a high sampling rate. In this manner, when the patient is not at rest, a higher relative sampling rate may be used to activate the pulse oximeter more often. The processor may return to performing the operations in block 502 to control the pulse oximeter at the default level measurement rate.

In response to determining that the patient is in a rest state (i.e., determination block 306="Yes"), the processor may set the measurement rate to a rest level in block 506. For example, the rest level may be a relatively lower measurement rate, such as a low sampling rate. In this manner, when the patient is at rest, fewer samples may be taken by the pulse oximeter, conserving battery power. The processor may return to performing the operations in block 502 to control the pulse oximeter at the rest state level measurement rate.

Figure 6:
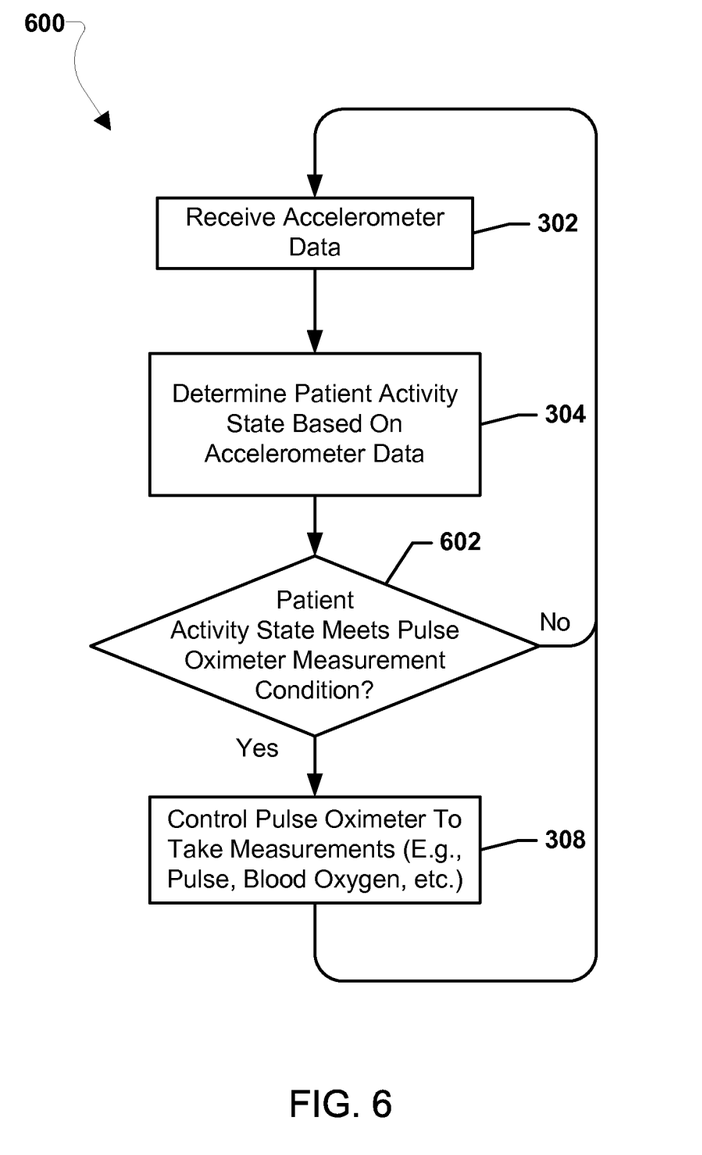
FIG. 6 is a process flow diagram illustrating an embodiment method for aligning pulse oximeter readings with a patient activity state based on accelerometer readings.

FIG. 6 illustrates an embodiment method 600 for aligning pulse oximeter readings with a patient activity state based on accelerometer readings. In an embodiment, the operations of method 600 may be performed by a processor of an electronic patch including a pulse oximeter and accelerometer, such as the patch 106 described above. As described above, in block 302 the processor may receive accelerometer data and in block 304 the processor may determine a patient activity state based on the received accelerometer data.

In determination block 602, the processor may determine whether a patient activity state meets a pulse oximeter measurement condition. In an embodiment, patient activity states may be correlated with instructions to take a pulse oximeter measurement. As examples, a patient entering a rest state may be correlated with taking a pulse oximeter measurement, a patient entering a high activity state may be correlated with taking a pulse oximeter measurement, and/or a patient reaching a maximum or peak activity rate may be correlated with taking a pulse oximeter measurement. In response to determining that the patient activity state does not meet a pulse oximeter measurement condition (i.e., determination block 602="No"), the processor may perform the operations in block 302 as described above. In response to determining that the patient activity state does meet a pulse oximeter measurement condition (i.e., determination block 602="Yes"), the processor may control the pulse oximeter to take measurements in block 308 as described above.

Figure 7:
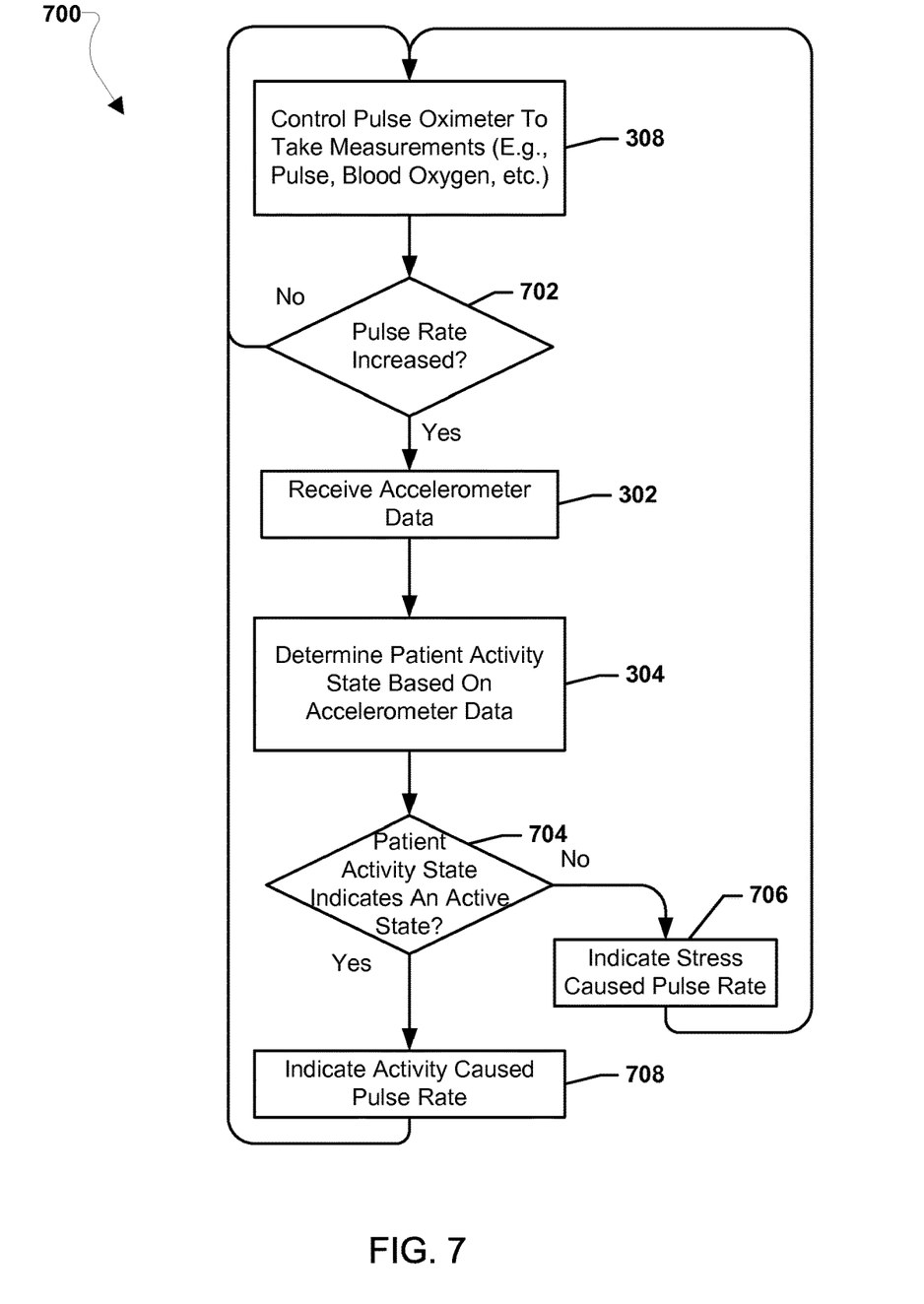
FIG. 7 is a process flow diagram illustrating an embodiment method for correlating heart rate increases with patient states.

FIG. 7 illustrates an embodiment method 700 for correlating heart rate increases with patient states. In an embodiment, the operations of method 700 may be performed by a processor of an electronic patch including a pulse oximeter and accelerometer, such as patch 106 described above. As described above, in block 308 the processor may control the pulse oximeter to take measurements, such as pulse rate measurements, blood oxygen measurements, etc. In block 702 the processor may determine whether the patient's pulse rate has increased. In response to determining the pulse rate has not increased (i.e., determination block 702="No"), the processor may return to performing the operations in block 308.

In response to determining the pulse rate has increased (i.e., determination block 702="Yes"), as described above, the processor may receive accelerometer data in block 302 and determine a patient activity state based on the received accelerometer data in block 304.

In determination block 704, the processor may determine whether the patient's activity state indicates an active state. In response to determining the patient activity state is not an active state (i.e., determination block 704="No"), the processor may indicate the pulse rate increase is caused by stress in block 706 and return to controlling the pulse oximeter in block 308. In response to determining that the patient is in an active state (i.e., determination block 704="Yes"), the processor may indicate the pulse rate increase is caused by patient activity in block 708 and return to controlling the pulse oximeter in block 308.

Figure 8:
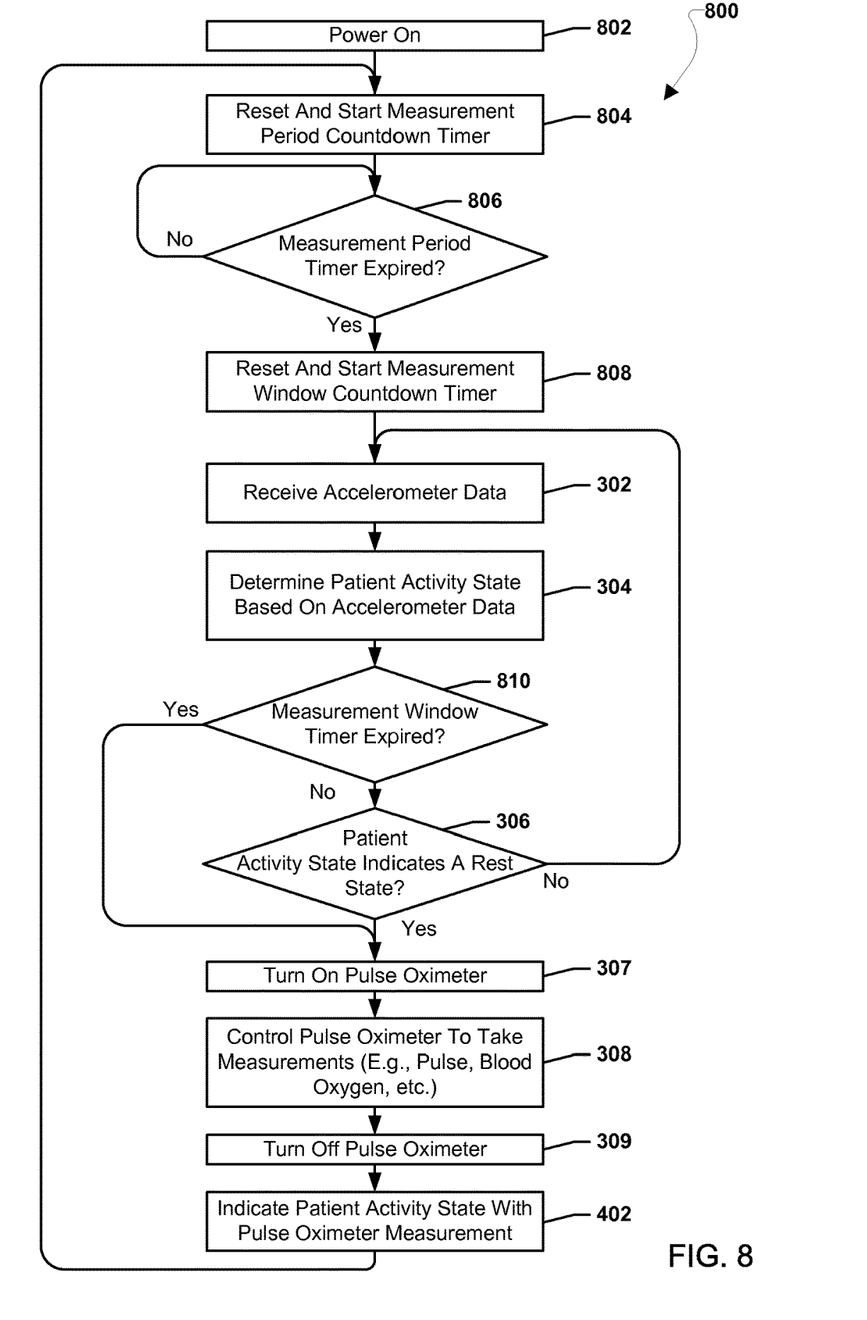
FIG. 8 is a process flow diagram illustrating another embodiment method for controlling a pulse oximeter based on a patient activity state indicated by accelerometer readings.

FIG. 8 illustrates an embodiment method 800 for controlling a pulse oximeter based on a patient activity state indicated by accelerometer readings. In an embodiment, the operations of the method 800 may be performed by a processor of an electronic patch including a pulse oximeter and accelerometer, such as the patch 106 described above. In block 802, the processor may be powered on. For example, the electronic patch may be removed from a wrapper and applied to a patient resulting in the processor of the electronic patch being powered on.

In block 804, the processor may reset and start a measurement period countdown timer. The measurement period countdown timer may be a countdown timer monitored by the processor that may be set to a minimum time to wait between performing pulse oximeter measurements. The minimum time to wait between performing pulse oximeter measurements may be set to any time value, such as less that 30 minutes, 30 minutes, more than 30 minutes, etc., and may vary based on patient medical conditions or any other factor.

In determination block 806, the processor may determine whether the measurement period countdown timer has expired. In response to determining that the measurement period countdown timer has not expired (i.e., determination block 806="Yes"), the processor may continue to monitor the status of the measurement period countdown timer and determine whether the measurement period countdown timer has expired in determination block 806.

In response to determining that the measurement period countdown timer has expired (i.e., determination block 806="Yes"), the processor may reset and start the measurement window countdown timer in block 808. The measurement window countdown timer may be a countdown timer monitored by the processor that may be set to a maximum time to wait for the patient to enter a rest state to perform a pulse oximeter measurement. The measurement window countdown timer may provide a maximum time to wait to attempt to take a more accurate pulse oximeter measurement during a patient rest state. After the measurement window countdown timer expires, the processor may default to taking a pulse oximeter measurement regardless of the current patient activity state. In this manner, a total period of time equal to the measurement period countdown timer plus the measurement window countdown timer may not be exceeded without taking a pulse oximeter measurement reading, regardless of the patient activity state. The maximum time to wait to attempt to take a more accurate pulse oximeter measurement during a patient rest state may be set to any time value, such as less that 10 minutes, 10 minutes, more than 10 minutes, etc., and may vary based on patient medical conditions or any other factor. After the wait time, the processor will default to taking a pulse oximeter measurement regardless of the current patient activity state.

In blocks 302 and 304 the processor may perform operations of like numbered blocks of the method 300 described above with reference to FIG. 3 to receive accelerometer data and determine a patient activity state. In determination block 808, the processor may determine whether the measurement window countdown timer has expired. In response to determining that the measurement window countdown timer has not expired (i.e., determination block 808="No"), the processor may determine whether the patient activity state indicates a rest state in determination block 306 as described above with reference to FIG. 3.

In response to determining that the patient is not in a rest state (i.e., determination block 306="No"), the processor may again receive accelerometer data in block 302 and determine a patient activity state in block 304.

In response to determining that the patient is in a rest state (i.e., determination block 306="Yes"), or in response to determining that the measurement window countdown timer has expired (i.e., determination block 808="Yes"), the processor may turn on the pulse oximeter in block 307, take measurements in block 308, and turn off the pulse oximeter in block 309 as described with reference to FIG. 3. In this manner, when the patient activity state is a rest state, or the maximum wait time is exceeded regardless of the patient activity state, the pulse oximeter may be activated to take a measurement, thereby conserving battery life by only powering on the pulse oximeter to take a measurement when the measurement is likely to be accurate or is needed to not miss a measurement window. In block 402, the processor may indicate the patient activity state with the pulse oximeter measurement as described with reference to FIG. 4. The processor may perform the method 800 in a loop by resetting and starting the measurement period countdown timer in block 804. In this manner, the pulse oximeter may only be turned on periodically to take measurements and thereby conserve battery life.

Figure 9:
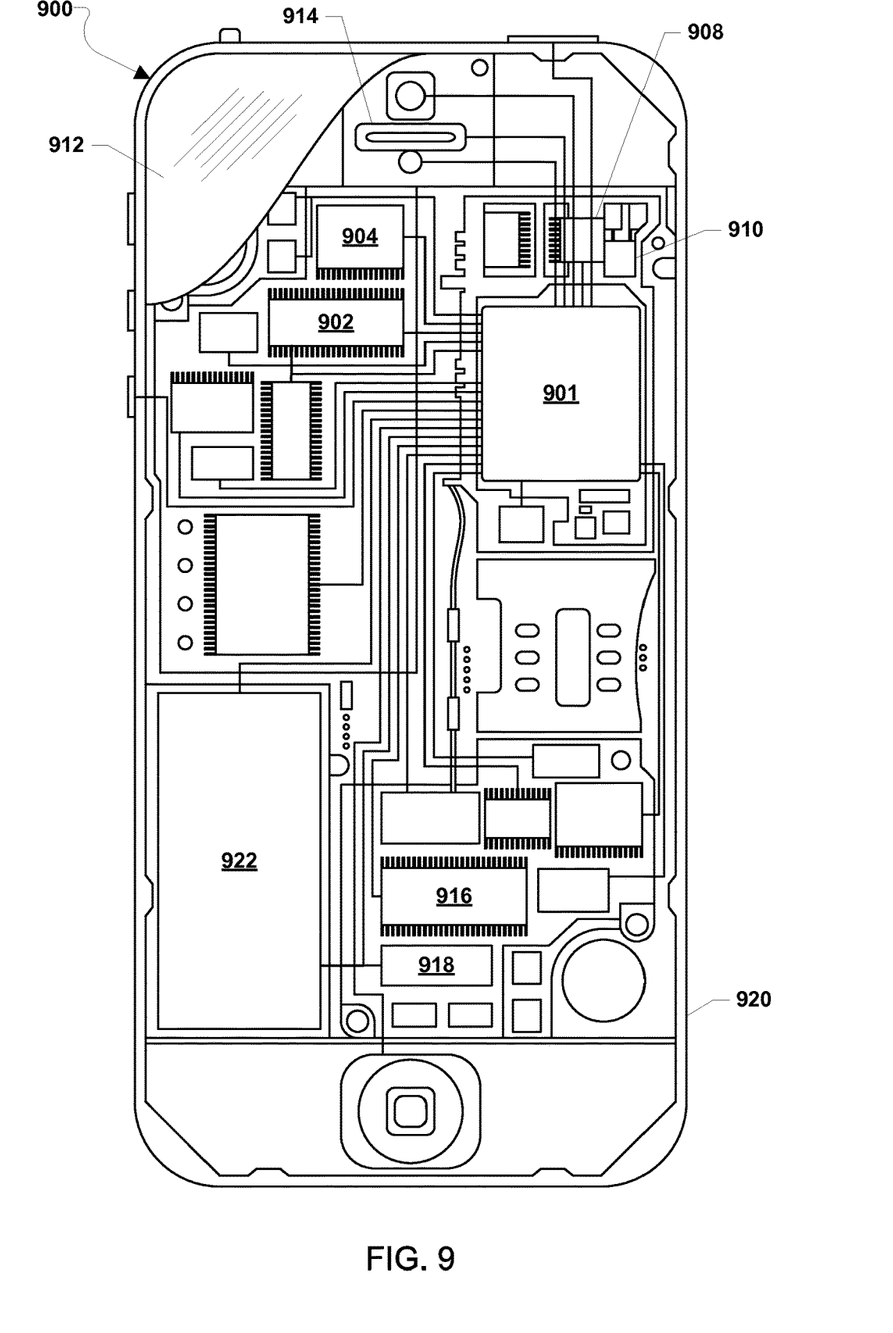
FIG. 9 is a component block diagram of a computing device suitable for use with the various embodiments.

An embodiment patch may be configured to transmit data to any of a variety of computing devices. For example, FIG. 9 illustrates a computing device 900 suitable for use in various embodiments. The computing device 900 may exchange data from the electronic patches discussed above, and may perform one or more of the operations of methods 300, 400, 500, 600, 700, and/or 800 described above. For example, accelerometer and/or pulse oximeter measurements may be sent to the computing device 900 and pulse oximeter control signals may be sent to the electronic patch from the computing device 900.

In various embodiments, the computing device 900 may include a processor 901 coupled to a touch screen controller 804 and an internal memory 902. The processor 901 may be one or more multicore ICs designated for general or specific processing tasks. The internal memory 902 may be volatile or non-volatile memory, and may also be secure and/or encrypted memory, or unsecure and/or unencrypted memory, or any combination thereof. The touch screen controller 904 and the processor 901 may also be coupled to a touch screen panel 912, such as a resistive-sensing touch screen, capacitive-sensing touch screen, infrared sensing touch screen, etc. The computing device 900 may have one or more radio signal transceivers 908 (e.g., Peanut®, Bluetooth®, Zigbee®, Wi-Fi, RF, cellular, etc.) and antennae 910, for sending and receiving, coupled to each other and/or to the processor 901. The transceivers 908 and antennae 910 may be used with the above-mentioned circuitry to implement the various wireless transmission protocol stacks and interfaces. The computing device 900 may include a cellular network wireless modem chip 916 that enables communication via a cellular network, such as an eMBMS network, and is coupled to the processor. The computing device 900 may include a peripheral device connection interface 918 coupled to the processor 901. The peripheral device connection interface 918 may be singularly configured to accept one type of connection, or configured to accept various types of physical and communication connections, common or proprietary, such as USB, FireWire, Thunderbolt, or PCIe.

The peripheral device connection interface 918 may also be coupled to a similarly configured peripheral device connection port (not shown). The computing device 900 may also include speakers 914 for providing audio outputs. The computing device 900 may also include a housing 920, constructed of a plastic, metal, or a combination of materials, for containing all or some of the components discussed herein. The computing device 900 may include a power source 922 coupled to the processor 901, such as a disposable or rechargeable battery. The rechargeable battery may also be coupled to the peripheral device connection port to receive a charging current from a source external to the computing device 900.

Processors of computing devices suitable for use in various embodiments may be any programmable microprocessor, microcomputer or multiple processor chip or chips that can be configured by software instructions (applications) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices, the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

Further, those of skill in the art will appreciate that the foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for controlling a pulse oximeter, comprising:
   receiving accelerometer data from an accelerometer coupled to the pulse oximeter;
   determining a patient activity state based at least in part on the received accelerometer data;
   determining whether the patient activity state is not a rest state;
   setting a sampling rate of the pulse oximeter to a first level based on whether the patient activity state is not a rest state,
   determining whether the patient activity state is a rest state;

setting the sampling rate of the pulse oximeter to a second level based on whether the patient activity state is a rest state, wherein the second level is a lower sampling rate than the first level; and controlling the pulse oximeter to take measurements in response to the determined patient activity state.

2. The method of claim 1, further comprising indicating the determined patient activity state with the pulse oximeter measurements.

3. The method of claim 1, wherein receiving accelerometer data from an accelerometer coupled to the pulse oximeter comprises:

determining whether a measurement period countdown timer has expired; and receiving accelerometer data from an accelerometer coupled to the pulse oximeter in response to determining that a measurement period countdown timer has expired.

4. The method of claim 1, wherein the accelerometer data are acceleration measurements or interrupts.

5. A device, comprising:

a pulse oximeter;

an accelerometer coupled to the pulse oximeter; and a processor coupled to the pulse oximeter and the accelerometer, wherein the processor is configured with processor executable instructions to perform operations comprising:

receiving accelerometer data from the accelerometer;

determining a patient activity state based at least in part on the received accelerometer data;

determining whether the patient activity state is a not rest state;

setting a sampling rate of the pulse oximeter to a first level based on whether the patient activity state is not a rest state, determining whether the patient activity state is a rest state; and setting the sampling rate of the pulse oximeter to a second level based on whether the patient activity state is a rest state, wherein the second level is a lower sampling rate than the first level; and controlling the pulse oximeter to take measurements in response to the determined patient activity state.

6. The device of claim 5, wherein the processor is configured with processor executable instructions to perform operations further comprising indicating the determined patient activity state with the pulse oximeter measurements.

7. The device of claim 5, wherein the accelerometer data are acceleration measurements or interrupts.

8. The device of claim 5, wherein the device is an electronic patch.

9. The device of claim 8, wherein the electronic patch further comprises a low power source coupled to the pulse oximeter, accelerometer, and processor.

10. The device of claim 9, wherein the low power source is a coin cell battery.

11. A non-transitory processor readable medium having stored thereon processor executable instruction configured to cause a processor to perform operations comprising:

receiving accelerometer data from an accelerometer coupled to a pulse oximeter;

determining a patient activity state based at least in part on the received accelerometer data;

determining whether the patient activity state is not a rest state;

setting a sampling rate of the pulse oximeter to a first level based on whether the patient activity state is not a rest state, determining whether the patient activity state is a rest state; and setting the sampling rate of the pulse oximeter to a second level based on whether the patient activity state is a rest state, wherein the second level is a lower sampling rate than the first level;

and controlling the pulse oximeter to take measurements in response to the determined patient activity state.

* * * * *